March 13, 1934. L. O. BONNET Plant Pat. 88

SEEDLESS GRAPE

Filed July 15, 1932

INVENTOR.
Leon O. Bonnet
BY
White, Prest, Flint & Lothrop
ATTORNEYS.

Patented Mar. 13, 1934

Plant Pat. 88

UNITED STATES PATENT OFFICE

88

SEEDLESS GRAPE

Leon O. Bonnet, Berkeley, Calif.

Application July 15, 1932, Serial No. 622,652

1 Claim. (Cl. 47—1)

This variety relates particularly to grapevines of the Vinifera type.

The general characteristics, care and propagation of the new variety of seedless grape of my origination are specifically set forth in the following description, while the accompanying drawing illustrates certain distinguishing characteristics of the new vine.

The vine, in general, is a hardy, vigorous and thrifty grower, having an abundant foliage of leaves of medium size, and is semi-erect. The new variety is a product of hybridization between the muscat of Alexandria and the Sultanina, the former being used as the mother vine and the latter as the father vine. The plant propagates from cuttings which graft and root well and is of good fertility, bearing on short pruning and producing medium size bunches of relatively large berries. As most Vinifera varieties, this new variety of seedless grape is susceptible to powdery mildew, having this fungus disease to about the same extent as the Sultanina (Thompson) seedless. Due to the fact that the berries do not readily become detached from the cap stem, that the bunch is somewhat loose, and also to the fact that the berries do not shatter, as does the Thompson seedless, the seedless grape of my discovery is of good shipping quality. Further, the grape gives promise of being of a good storage quality.

Figure 1:
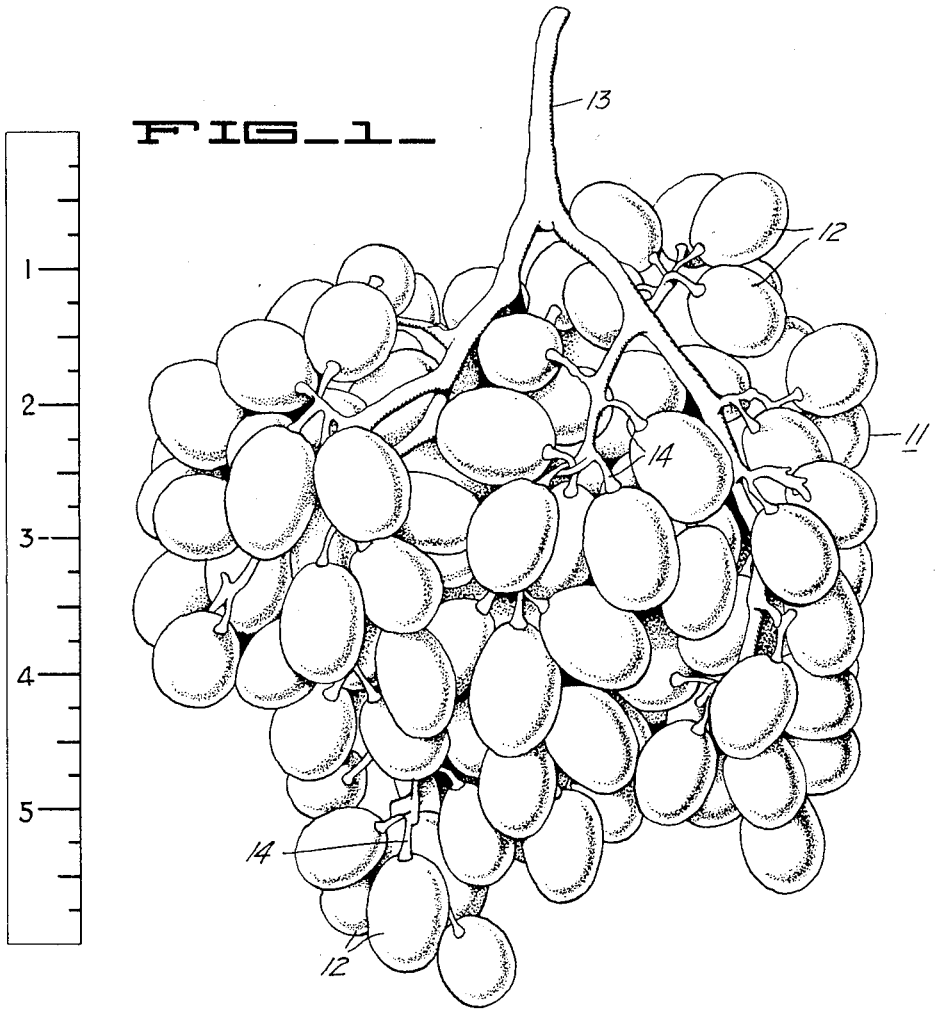
Figure 1 is a view of a typical bunch of grapes from the vine of my origination and representing the actual size and shape of the berries and bunch.

The berries produced by the new variety of vine are of a greenish tint at full maturity and can be said to have a neutral flavor, as it is not sufficiently pronounced to be classified among grape aromas, although the flavor is of sprightly character. In color, therefore, the berry of the new vine is distinguishable from the berry of the Sultanina since the latter is amber in color at full maturity. As illustrated in Figure 1, which represents the actual size and shape of a bunch 11 of grapes 12 produced by the vine, the berry 12 is relatively large, measuring approximately 23x18 millimeters, and is of generally ellipsoidal shape. The pulp of the berry is of medium texture but not juicy, and the seeds are substantially absent, although two or three soft, partly developed seeds were found to be present in the berry. The fact that these seeds are no tougher than the skin of the berry makes this variety a seedless. The grapes of this new vine are not astringent.

With further reference to Figure 1, it will be observed that the bunch 11 is of medium size and is somewhat pyramidal in shape, being relatively short in length but thick at the base thereof. The bunch is relatively dense with berries throughout its entirety. The peduncle 13 is reddish-green in color, is of medium size, and is medium hard in texture. The pedicels 14 are relatively long, are of greenish color and of medium texture, and, I have found, adhere firmly to the berry.

Figure 2:
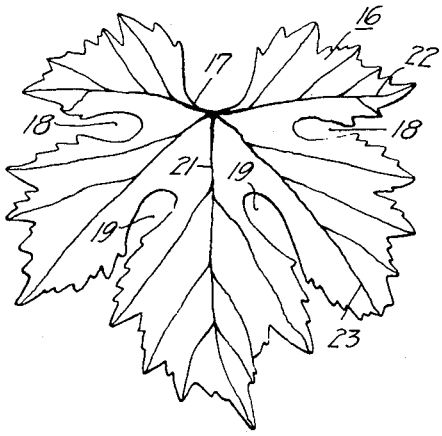
Figure 2 is a plan of a typical leaf of the new variety of vine, this view representing one-half the actual size of the leaf.

An outstanding distinguishing characteristic of this new variety of grapevine is its unusual leaf. I have illustrated in Figure 2 of the drawing a leaf 16 taken from the vine, upon reference to which it will be noted that while the leaf generally is of medium size, the ratio of length to width is slightly superior to one. The typical leaf measures about 16 centimeters by 15.5 centimeters, and is deeply five-lobed, as shown. The leaf of the Sultanina is not deeply five-lobed. The petiolar sinus 17 is of general U-shape which is not true of the petiolar sinus of the Sultanina leaf and, while the lower sinuses 18 are deep and sometimes closed, the upper sinuses 19, although also deep, are generally open. Further, the main median vein 21 forms angles of approximately 98° and 48°, respectively, with the outside vein 22 and inside vein 23 on the right side of the leaf. I have observed that the lower side of the leaf is pubescent on all of the veins and that the leaf is of a generally light greenish color, resembling, in this latter respect, the leaf of the Thompson seedless. The leaf of the Sultanina vine is not pubescent on its lower side.

I have found that the seedless grape of my origination will grow well in the interior valleys of California, that is, in the Sacramento and San Joaquin Valleys and, hence is substantially of the same resistance to cold, drought and heat as other varieties. The grape ripens at about the time of the second period of the Thompson seedless. In view of the fact that the seedless of my discovery has substantially all of the characteristics of not only the table and raisin grape but also some of the characteristics of the wine grape, the new seedless is of substantial value. It is similar to the table grape in that it has relatively large berries, a special taste including sweetness and, further, it has good shipping qualities and presents a firm appearance for relatively long periods because it does not shatter readily. Because of the absence of seeds and also of the size and flavor of the berry, the new variety furnishes an excellent layer raisin. While the foregoing are perhaps the two principal uses of the new grape, it may be used also as a wine grape.

I claim:

A seedless grape of the character herein described, the vine being characterized by its semi-erect growth and by its bearing of generally pyramidal shape clusters of relatively large and substantially seedless berries which are of greenish tint at full maturity; the vine being further characterized by its deeply five-lobed leaves which are pubescent on all veins on their lower sides, and by the fact that the petiolar sinus of each leaf is of general U-shape.

LEON O. BONNET.